US006472208B1

(12) United States Patent
Lemieux et al.

(10) Patent No.: US 6,472,208 B1
(45) Date of Patent: Oct. 29, 2002

(54) METHOD OF PRODUCING HUMAN IFN-α USING SENDAI VIRUS-INFECTED HEMATOPOIETIC STEM CELLS

(75) Inventors: Réal Lemieux, Sainte-Foy (CA); Sonia Néron, Sainte-Augustin (CA); Chantal Proulx, Sainte-Foy (CA)

(73) Assignees: Héma-Québec (CA); Canadian Blood Services (CA)

( * ) Notice: Subject to any disclaimer, the term of this patent is extended or adjusted under 35 U.S.C. 154(b) by 0 days.

(21) Appl. No.: 09/612,583

(22) Filed: Jul. 7, 2000

Related U.S. Application Data

(60) Provisional application No. 60/170,354, filed on Dec. 13, 1999.

(51) Int. Cl.$^7$ .......................... C12N 15/85; C12N 15/86
(52) U.S. Cl. ...................... 435/325; 424/93.1; 530/351
(58) Field of Search .................. 435/325; 530/351; 424/93.1

(56) References Cited

U.S. PATENT DOCUMENTS 5,436,151 A * 7/1995 McGlave et al. ......... 435/240.1
6,288,030 B1 * 9/2001 Hershenson et al. .......... 514/12

OTHER PUBLICATIONS

J.E. Banatvala et al. Interferon response to Sendai and Rubella viruses in human foetal cultures, leucocytes and placental cultures. 1971. J. Gen. Virol., 13:193–201.*
I. Splichal et al. Ontology of interferon alpha secreting cells in the porcine fetal hematopoietic organs. 1994. Immunol. Lett., 43:203–208.*
Arrighi, J.F., et al., *Blood*, 93(7): p. 2244–2252, 1999.
Baron, S., et al., *Journal of American Medicine Association*, 266(10), p. 1375–1383, 1991.
Brandt, E.R., et al., *Br J Haematol*, 86(4): p. 717–725, 1994.
Brugger, W., et al., *N Engl J Med*, 333(5): p. 283–287, 1995.
Cantell, K., S., et al., *Methods Enzymol*, 78(Pt): p. 499–505, 1981.
Cantell, K., S., et al., *Methods Enzymol*, 78(Pt): P. 29–38, 1981.
Collins, P.C., et al., *Biotechnol Bioeng*, 59(5): p. 534–543, 1998.
Eloranta, M.L., et al., *Scand J Immunol*, 46(3): p. 233–241, 1997.
Feldman, S.B., et al., *Virology*, 204(1): p. 1–7, 1994.
Hart, D.N., *Blood*, 90(9): p. 3245–3287, 1997.
Hu, W.S. and J.G. Aunins, *Curr Opin Biotechnol*, 8(2): p. 148–153, 1997.
Nyman, T.A., et al., *Biochem J*, 329(Pt2): p. 295–302, 1998.
Pfeffer, L.M. et al., *Cancer Res*, 58(12): p. 2489–99, 1998.
Pfeffer, L.M., *Semin Oncol*, 24(3 Suppl 9): p. S9–63–S9–69, 1997.
Piacibello, W., et al., *Blood*, 89(8) p. 2644–2653, 1997.
Romani, N., et al., *J Exp Med*, 180(1): p. 83–93, 1994.
Sandstrom, C.E., et al. *Blood*, 86(3): p. 958–970, 1995.
Siegal, F.P., et al., *Science*, 284(5421): p. 1835–1837, 1999.
Svensson, H., et al., *Scand J Immunol*, 44(2): p. 164–172, 1996.
Traycoff, C.M. et al., *Exp Hematol*, 26(1): p. 53–62, 1998.
Zandstra, P.W., et al., *Biotechnology* (NY), 12(9): p. 909–914, 1994.
Zandstra, P.W., et al., *Proc Natl Acad Sci U S A*, 94(9): p. 4698–4703, 1997.
Ziegler, B.L. and L. Kanz, *Curr Opin Hematol*, 5(6): p. 434–440, 1998.

* cited by examiner

*Primary Examiner*—Lorraine Spector
*Assistant Examiner*—Dong Jiang
(74) *Attorney, Agent, or Firm*—Nixon Peabody LLP

(57) ABSTRACT

The present invention relates to a novel method for producing human natural interferon-α using ex vivo expanded cord blood hematopoietic cells infected with sendaivirus, on a large scale.

5 Claims, 1 Drawing Sheet

METHOD OF PRODUCING HUMAN IFN-α USING SENDAI VIRUS-INFECTED HEMATOPOIETIC STEM CELLS

This application claims benefit of Prov. app. 60/170,354 filed Dec. 13, 1999.

BACKGROUND OF THE INVENTION (a) Field of the Invention

The invention relates to a novel method for producing human natural interferon-α using ex vivo expanded cord blood hematopoietic cells.

(b) Description of Prior Art

Interferons (IFNs) are a class of cytokines with pleiotropic biological activities (Pfeffer, L. M. et al., *Cancer Res*, 58(12): p. 2489–99, 1998). Originally described as potent anti-viral agents, IFNs are now known to also have antiproliferative and immunomodulatory activities. IFNs are classified as Type I and Type II depending on their structure and stability in acid medium. Type I IFNs are subclassified by homology of amino acid sequence and type of producing cells as IFN-α (leukocytes), IFN-β (fibroblasts) and IFN-ω (leukocytes). Type II IFN is acid-labile and comprises only IFN-γ produced by activated T cells and NK cells. In opposition to IFN-β and IFN-γ, IFN-α is molecularly heterogeneous and comprises at least 13 proteins coded by more than 14 genes (Pfeffer, L. M., *Semin Oncol*, 24(3 Suppl 9): p. S9-63–S9-69, 1997). The similarity between the IFN-α proteins is between 78% and 95% at the protein level and 79/166 amino acids are conserved in the family. Furthermore allelic forms of IFN-α genes with variations in 1 to 4 amino acids have been described thus greatly increasing the number of potential IFN-α proteins (Nyman, T. A., et al., *Biochem J*, 329(Pt 2): p. 295–302, 1998). The exact reason for the existence of so many IFN-α species remains unclear since all species exhibit the same biological activities. However the specific activities of each species in different biological assays vary greatly by a factor up to 1000-fold and this observation could be related in some cases to differences in affinity of the various IFN-α species for the receptor (IFN-αR) expressed on various cells (Pfeffer, L. M., *Semin Oncol*, 24(3 Suppl 9): p. S9-63–S9-69, 1997). It remains to be seen if the mixture of IFN-α species varies according to the producing cells or the inducing agent.

In the 1970s, the anti-proliferative activity of Type I IFNs attracted much interest for potential use in cancer treatment. At that time, the available IFN-α was natural (nIFN-α) and produced mainly by overnight culture of pooled human blood leukocytes after infection with Sendai virus following protocols developed by the group of Cantell in Helsinki (Cantell, K., S., et al., *Methods Enzymol*, 78(Pt): p. 29–38, 1981). This preparation of nIFN-α has been recently shown to contain at least 9 of the known IFN-α species (Nyman, T. A., et al., *Biochem J*, 329(Pt 2): p. 295–302, 1998). The molecular cloning of the first IFN-α cDNA (species 2a) in 1979 shifted the interest to recombinant molecules (rIFN-α) produced in bacteria because of the possibility of large supply which was difficult to achieve with the leukocyte-derived nIFN-α. In 1987, the first rIFN-α was approved by the FDA for use in the treatment of hairy cell leukemia. This rIFN-α2a molecule was followed shortly after by a rIFN-α2b species (Baron, S., et al., *Journal of American Medicine Association*, 266(10), p. 1375–1383, 1991). Today the rIFN-αs are widely used in the treatment of more than 10 malignancies and virologic diseases including the widespread hepatitis B and C infections (Pfeffer, L. M. et al., *Cancer Res*, 58(12): p. 2489–99, 1998). However therapeutic use rIFN-α results in clinical improvement in only a fraction of the patient populations. For example, the rIFN-α treatment of Hepatitis C-infected patients is highly effective only in 30% of the cases. Significant side effects of rIFN-α injection are routinely observed and may prevent the long-term treatment necessary to eradicate the virus. Also a significant proportion of IFN-α-treated patients (10–20%) develop antibody inhibitors which may interfere with the therapeutic effect or prevent continuous treatment. These limitations and side effects and the fact that the two available rIFN-α species (2a and 2b) may not be the most effective IFN-α species in some diseases have renewed the interest in the nIFN-α preparations. Indeed less side effects and frequency of antibody inhibitors formation have been observed in some small scale clinical trials. Also the switch from rIFN-α to nIFN-α could permit to prolong the treatment of patients which have developed a resistance to rIFN-α. With the same objectives, a synthetic rIFN-α termed rIFN-α-con1 has been designed in vitro by assigning at each position in the primary sequence, the amino acid most frequently observed in several IFN-α species. The rIFN-α-con1 is also tested in clinical trials.

The nIFN-α is currently produced by overnight culture of Sendai virus-infected human leukocytes isolated from the buffy coats prepared from several hundred blood donations (Cantell, K., S., et al., *Methods Enzymol*, 78(Pt): p. 29–38, 1981). This procedure has several limitations. On one hand, it requires tight logistics with the blood bank since production of nIFN-α must be done with fresh cells and initiated within 24 hours of blood collection. In this regard, the increasing use of pre-storage leukodepletion by filtration to reduce contamination of red blood cells and platelets by leukocytes will further increase the difficulties in recovering leukocytes for nIFN-α production. On the other hand, lots of nIFN-α must be prepared from pools of leukocytes prepared from thousands of blood donations. Although the nIFN-α can be highly purified and subjected to viral inactivation procedures, there are concerns about possible contamination of the final product with untested or unknown infectious agents.

Much work has been done to characterize the IFN-α producing cells present in the peripheral blood. Early results showed that the major IFN-α producing cells constituted only a minor portion of blood leukocytes (Feldman, S. B., et al., *Virology*, 204(1): p. 1–7, 1994; and Brandt, E. R., et al., *Br J Haematol*, 86(4): p. 717–725, 1994). Subsequent work showed that these cells possessed markers characteristic of immature monocyte/dendritic cells (Eloranta, M. L., et al., *Scand J Immunol*, 46(3): p. 235–241, 1997; and Svensson, H., et al., *Scand J Immunol*, 44(2): p. 164–172 1996). Recently a major IFN-α-producing cell in blood was isolated and shown to have markers characteristics of lymphoid dendritic cells (DC) precursors (CD4+CD11c−) (Siegal, F. P., et al., *Science*, 284(5421): p. 1835–1837, 1999). Dendritic cells are terminally differentiated lymphoid and myeloid cells that have important immunomodulatory roles in antigen presentation and cytokine secretion. Mature DCs are constantly produced from both lymphoid and myeloid precursors (Hart, D. N., *Blood*, 90 (9): p. 3245–3287, 1997). One strategy to increase the nIFN-α productivity of blood leukocytes would be to expand the IFN-α-producing cells in vitro prior to IFN-α induction with Sendai virus. Culture conditions (GM–CSF+IL4) that permits to expand the blood DCs have been described but the expansion factor remained limited (10–20×) (Romani, N., et al., *J Exp Med*, 180(1): p. 83–93, 1994). Also the presence of cytotoxic T lymphocytes would prevent the pooling of the leukocytes from different donors for the culture expansion phase. However hematopoietic stem cells (HSCs) can now be expanded in vitro for several weeks (Piacibello, W., et al., *Blood,* 89(8): p. 2644–2653, 1997; Traycoff, C. M., et al., *Exp Hematol,* 26 (1): p. 53–62, 1998; and Ziegler, B. L. and L. Kanz, *Curr Opin Hematol,* 5(6): p. 434–440, 1998). In these cultures, the HSCs proliferate and differentiate autonomously into progenitors of the various blood cell lineages. But in most instances, differentiation of HSCs is not complete and does not proceed to the mature blood cell stage in these cultures (Ziegler, B. L. and L. Kanz, *Curr Opin Hematol,* 5(6): p. 434–440, 1998).

It would be highly desirable to be provided with a method for producing human natural interferon-α on a large scale.

SUMMARY OF THE INVENTION

One aim of the present invention is to provide a method for producing human natural interferon-α on a large scale using ex vivo hematopoietic stem cells such as cord blood hematopoietic cells.

In accordance with the present invention there is provided a process for producing ex vivo natural interferon α (nIFN-α) from cultured hematopoietic stem cells (HSCs) infected with Sendai Virus.

Still in accordance with the present invention, there is provided a method for producing ex vivo natural interferon α (nIFN-α). The method comprises the steps of:

a) infecting hematopoietic stem cells (HSCs) in culture medium with Sendai Virus; and b) culturing the HSCs of step a) for a time sufficient for the HSCs to produce nIFN-α.

The method of the present invention may further comprise before step a) the step of expanding under suitable conditions the HSCs in culture.

In another embodiment of the present invention, the method may further comprise before step a) and after the step of expanding, a step of pooling expanded HSCs obtained from the step of expanding.

The method of the present invention may further comprise before step a) and after the step of expanding if any, the step of priming the HSCs for nIFN-α secretion by incubating the HSCs in IFN-α.

The method of the present invention may further comprise after step b), a step of collecting from the culture medium the natural nIFN-α obtained from step b).

Preferably, the HSCs are from cord blood. Also, the HSCs are preferably enriched in CD34+.

In accordance with the present invention, there is also provided a natural interferon-α produced by the method described above.

DETAILED DESCRIPTION OF THE INVENTION

Figure 1:
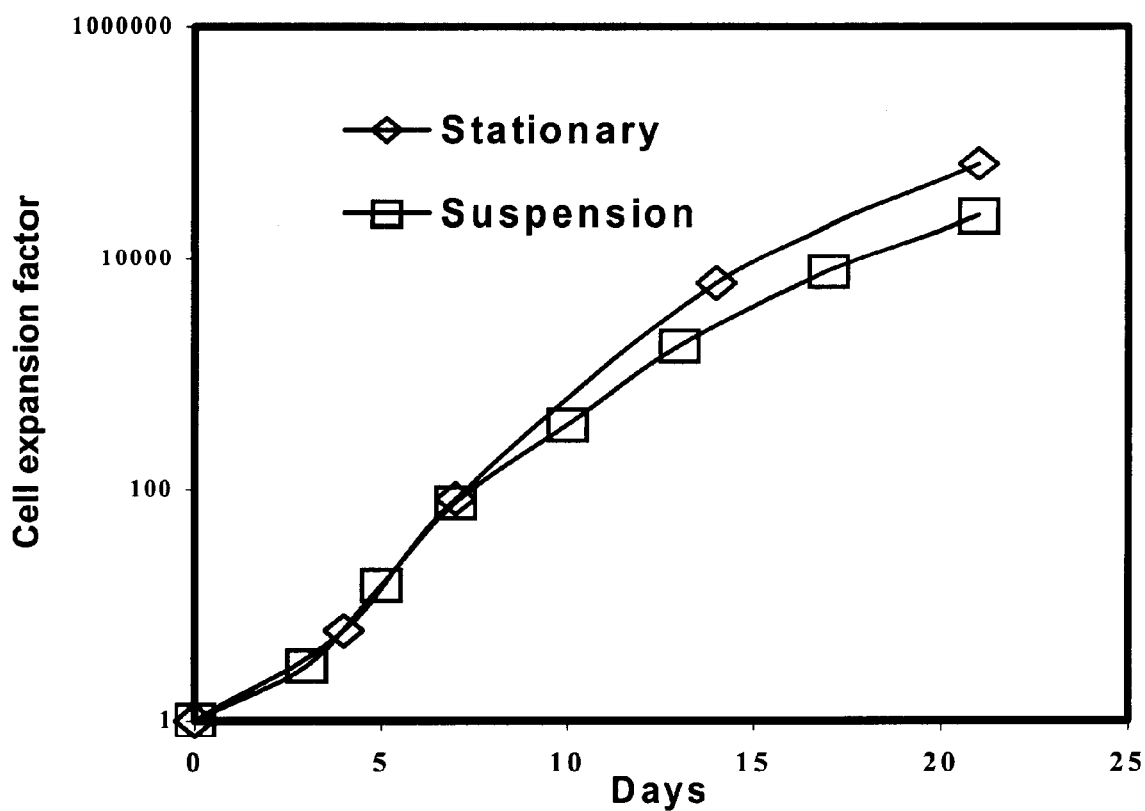
FIG. 1 illustrates a scattergram plot of cumulative ex vivo expansion of hematopoietic cells from cord blood CD34+-enriched progenitor cells either in stationary (◊) or in suspension (□) culture, in accordance with one embodiment of the present invention.

Since IFN-α is produced mainly by immature DCs and possibly other blood cells, it was found that the frequency of IFN-α-producing cells is higher in cultured hematopoetic cells (HCs) than in peripheral blood leukocytes. In the present invention, it is shown that HCs prepared by culture in suspension of HSCs isolated from cord blood produced much more IFN-α than blood leukocytes on a per cell basis. The use as starting material, of HSCs from cord blood instead of from bone marrow or peripheral blood also permitted the pooling for the expansion phase, of the HSCs from several donors due to the immaturity of the immune system of the newborns. The observed high nIFN-α productivity and large expansion of HCs in suspension cultures (>2.5×10$^4$) make it possible to consider the industrial production of nIFN-α starting from pooled HSCs isolated from a limited number of cord blood samples.

HSCs were cultured using previously described procedures. Briefly, CD34+ HSCs were enriched about 50-fold (44±12%) by negative selection of the cord blood mononuclear cells (0.5–1.0% CD34+). The enriched CD34+ HSCs were cultured at low cell seeding densities (<10$^5$/ml) in a serum-free medium supplemented with albumin, transferrin, insulin, IL-3, IL-6, G-CSF, Flt3 (a factor ligand) and SCF (stem cell factor) as previously described (Zandstra, P. W., et al., *Proc Natl Acad Sci USA,* 94(9): p. 4698–4703, 1997). In these conditions, the total number of cells continuously increased over a three weeks period yielding a cumulative expansion of more than 6×10$^4$ fold in stationary cultures (FIG. 1). The expansion factor was calculated from the viable cell counts and the culture dilution ratio done at the indicated time points. As expected (Brugger, W., et al., *N Engl J Med,* 333(5): p. 283–287, 1995; and Sandstrom, C. E., et al., *Blood,* 86(3): p. 958–970, 1995), most of the expanded cells no longer expressed the CD34 HSC marker (<1%) indicating the initiation of differentiation long the various blood cell lineages. To facilitate scale-up, the inventors have investigated the possibility of expanding the HCs in suspension cultures. Preliminary experiments indicated that the HSCs would not initiate proliferation in suspension cultures at the low cell seeding used in stationary cultures. However, by maintaining cell density higher than 2.5×10$^5$ cells/ml, a continuous expansion was obtained for the 21 day culture period with a factor of about 2.5×10$^4$ fold (FIG. 1). In those experiments, it was also observed that the HSCs isolated from the cord blood of several newborns could be pooled for the culture phase without affecting the expansion factor.

Cultured HCs and freshly prepared blood leukocytes were compared for their ability to secrete nIFN-α following infection with Sendai virus. Induction of nIFN-α secretion by infection of blood leukocytes with Sendai virus has been used industrially for many years and the optimal experimental conditions have been described in details (Cantell, K., S., et al., *Methods Enzymol,* 78(Pt): p. 29–38, 1981). Briefly, fresh leukocytes present in buffy coats collected from centrifuged blood were washed, pooled and freed of red blood cells by NH$_4$Cl lysis. The leukocytes were cultured at 37° C. in suspension cultures at 1×10$^6$ cells/ml and first primed with a low concentration of IFN-α prior to infection with Sendai virus. After overnight culture, the supernatant is collected and the nIFN-α content is assayed by ELISA. The same protocol for nIFN-α induction was used for both blood leukocytes and cultured HCs. The nIFN-α yields of the various cell populations are listed in Table 1. Fresh leukocytes isolated either from adult peripheral blood or cord blood produced about 2.1 IU of IFN-α per 10$^3$ cells. Under similar induction conditions, the unselected cord blood leukocytes and the CD34+-enriched HSCs produced less nIFN-α with yields of 0.53 and 1.1 IU per 10$^3$ cells respectively. However, the HCs produced by expansion of the cord blood HSCs in suspension cultures produced about 14 times more nIFN-α with an average of 28.9 IU/10³ cells. This result indicated that the ability of cord blood mononuclear cells HSCs to secrete nIFN-α greatly increased about 30-fold during the culture phase.

TABLE 1

Comparative yield of nIFN-α from Sendai virus-infected blood leukocytes and hematopoietic cells (HCS)

| | | Yield of nIFN-α IU/10³ cells | |
|---|---|---|---|
| Source of Cells | Total Leukocytes | CD34⁺-enriched HSCs | Cultured HCs |
| Peripheral Blood | 2.1 ± 0.3[1] | — | — |
| Cord Blood | 0.53 | 1.1 | 28.9 ± 11[2] |

[1]mean of 3 independent experiments (1.9–2.5)
[2]mean of 3 independent experiments (10.3–36.8 range) using three different pools of cord blood samples (2–6 samples/pool)

To better evaluate the potential benefits of using cultured HCs instead of fresh adult blood leukocytes for nIFN-α production, the yield of nIFN-α that could be derived from a single unit of cord blood or adult peripheral blood was calculated. Results are summarized in Table 2 and show that the 23,000-fold cell expansion factor observed in suspension cultures compensated for the relatively low number of HSCs present in one cord blood unit ($3 \times 10^6$ cells). This expansion coupled with the higher nIFN-α specific productivity of the cultured HCs, indicated that the total amount of nIFN-α that can be produced from a single cord blood donation ($2 \times 10^9$ IU) is similar to the amount derived from the pooled fresh leukocytes present in about 1000 regular blood donations (450 ml). With the higher expansion observed in stationary cultures, the corresponding number of regular blood donations is close to 2,500.

TABLE 2

Cells and nIFN-α yields per unit of starting blood donation

| | Source of IFN-α producing cells | |
|---|---|---|
| Yields | Peripheral Blood | Cord Blood |
| Unit Volume | 450 ml | 75 ml |
| Number of Cells after isolation | $1 \times 10^9$ (leukocytes) | $3 \times 10^6$ (CD34⁺) |
| after culture | — | $6.9 \times 10^{10}$ |
| nIFN-α, IU | $2.1 \times 10^6$ | $2.0 \times 10^9$ |

The application of ex vivo expansion of HSCs have been until now targeted to the preparation of a high number of stem and progenitor cells for transplantation, supportive treatments and gene therapy. The results obtained with the present invention indicate that the cultured HC could also be useful in the manufacturing of complex biologicals such as IFN-α which are difficult to produce in their natural form by recombinant DNA technology. The higher IFN-α specific productivity of HCs is the main factor that permits to consider the use of HCs in replacement of blood leukocytes. The overall IFN-α productivity of HCs could possibly be further increased significantly by optimizing the culture conditions for the expansion of IFN-α producing-cells. In the experiment that led to the present invention, a mixture of cytokines that has been optimized for expansion of HSCs and multi-lineage progenitors was used. Different mix of cytokines have been shown to preferentially target differentiation of particular cell lineages including the DC pathway which was favored by a cytokine mixture containing TPO (thrombopoietin), SCF and FL (factor ligand) (Arrighi, J. F., et al., *Blood*, 93(7): p. 2244–2252, 1999). This strategy is supported by the observation that the viability in HCs cultures remained high (>75%) at the end of the IFN-α secretion period (18 hours after Sendai virus infection) suggesting that most cultured HCs were not at the differentiation stage or of the cell lineage suitable for massive Sendai virus-induced IFN-α production.

The use of cord blood-derived HCs for IFN-α production has several advantages over the current methods of the prior art based on fresh blood leukocytes. First, the logistics of the nIFN-α production process would be much simplified since the HSCs and derived HCs can be stored frozen before or during expansion in opposition to the blood leukocytes which must be used fresh and within 24 hours of blood collection. Another related advantage is the possibility of pooling the HSCs from several cord blood samples prior to the culture phase. This procedure would permit the preparation of large cell banks which could be first extensively characterized for nIFN-α yield and absence of infectious agents and then used for production of many IFN-α lots as routinely done in production processes based on the use of cell lines secreting other biologicals. Another clear advantage is that the final nIFN-α product would be derived from a much smaller (>1000 fold less) pool of blood donations than the peripheral blood-derived product. Although current blood screening procedures used in all blood banks are efficient in the detection of several infectious agents, the use of biologicals derived from a pool of thousands of blood donations increases the risk of transmission of unknown or untested infectious agents.

The main technological challenge associated with the use of cultured HCs in nIFN-α production is the scale-up of the culture system. HSCs have been previously cultured efficiently in small bioreactor systems (Collins, P. C., et al., *Biotechnol Bioeng*, 59(5): p. 534–543, 1998; and Zandstra, P. W., et al., *Biotechnology* (N Y), 12(9): p. 909–914, 1994) but the large number of HCs necessary for industrial production of nIFN-α would require larger systems. In the present invention, the volume of HC culture generated after the 21 day expansion phase of the HSCs isolated from a single cord blood sample would be about 40–50 liters. Although the procedure could be done in roller bottles, the efficiency of the process could be much higher in bioreactors. Bioreactors operating in the perfusion mode (Hu, W. S. and J. G. Aunins, *Curr Opin Biotechnol*, 8(2): p. 148–153, 1997) would be ideally suited for this purpose since the composition of the culture medium (e.g. cytokines) could be modified during the expansion phase to favor the differentiation in IFN-α-producing cells and to permit the in situ induction of nIFN-α production by Sendai virus injection at the end of the expansion phase. In preliminary experiments of discontinuous perfusion, the inventors have observed that the viable HCs density in suspension cultures could be increased from $1.5 \times 10^6$ to $10^7$ cells/ml by changing half the culture volume each day after centrifugation of the HCs. Additional work will permit to better define the bioreactor type that is optimal for this purpose but the objective can be met with the large scale cell culture technologies available at the present time.

The present invention will be more readily understood by referring to the following examples, which are given to illustrate the invention rather than to limit its scope.

EXAMPLE 1
Preparation Of Blood Leukocytes

Buffy coats isolated from 9 to 12 blood donations were pooled and processed within 24 hours of blood collection as previously described (Cantell, K., S., et al., *Methods Enzymol,* 78(Pt): p. 29–38, 1981). Briefly, the residual red blood cells were lyzed by adding 3 volumes of 0.83% ammonium chloride. After centrifugation, the leukocytes were resuspended in phosphate-buffered saline (PBS) (0.15M NaCl, 0.015M sodium phosphate pH 7.2). Viability ranged from 85% to 95% by Trypan blue exclusion.

EXAMPLE 2
Culture Of Hematopoietic Cells

Mononuclear cells (MNCs) were isolated from freshly collected cord blood by centrifugation over Ficoll-Hypaque™ (Amersham Pharmacia Biotech, Uppsala, Sweden). The MNCs were washed in PBS by centrifugation and, unless otherwise noted, were stored frozen at $-150°$ C. in Iscove's modified Dulbecco medium (IMDM) containing 40% fetal bovine serum (FBS) (Life Technologies, Rockville, Md., USA) and 10% dimethyl sulfoxide) (DMSO) (Sigma Chemicals, St-Louis, Mo.). For the enrichment of $CD34^+$ HSCs, the thawed MNCs were diluted in 10 volumes of IMDM containing 20% FBS and 0.1 mg/ml of DNAse (Sigma). After centrifugation, the cells were resuspended in PBS containing 5% FBS and 0.1 mg/ml DNAse. Average viability was 85% by Trypan blue exclusion. Cell concentration was adjusted to $2-8\times10^7$ cells/ml and the CD34+ HSCs were enriched using the StemSep™ Cell Separation System (Stem Cell Technologies, Vancouver, Canada) according to the manufacturer's instructions. The enriched $CD34^+$ HSCs present in the column flowthrough represented $0.77\pm 0.6\%$ of the starting MNC population. The $CD34^+$ cells were cultured as described by Zandstra et al. (Zandstra, P. W., et al., *Proc Natl Acad Sci USA,* 94(9): p. 4698–4703, 1997) with some modifications. Briefly cells were incubated at $37°$ C. in 1.25 ml stationary (24 well microplate) or suspension (rolling $12\times 75$ mm tubes cultures. The IMDM culture medium was supplemented with the 20% BIT serum substitute (Stem Cell Technologies), low density lipoproteins (4 μg/ml) (Sigma), 2-mercaptoethanol ($5\times 10^{-5}$M) (Sigma) and recombinant human cytokines (R&D Systems, Minneapolis, Minn., USA): IL-3 (20 ng/ml), G-CSF (20 ng/ml), IL-6 (20 ng/ml), SCF (100 ng/ml) and Flt3/Flk2 ligand (FL) (100 ng/ml). Cultures were initiated at about $5\times 10^4$ cells/ml (stationary) or at $2.5\times 10^5$ cells/ml (suspension). Adjustment of the cell density to about $5\times 10^4$ cells/ml (stationary) or $2.5\times 10^5$ cells/ml (suspension) was done every 7 days (stationary) or 2–4 days (suspension) by removing a portion of the culture and replacing it with fresh culture medium.

EXAMPLE 3
Induction of IFN-α Production with Sendai Virus

Infection with Sendai virus was done as previously described (Cantell, K., S., et al., *Methods Enzymol,* 78(Pt): p. 29–38, 1981; and Cantell, K., et al., *Methods Enzymol,* 78(Pt): p. 499–505, 1981). Peripheral blood-derived leukocytes and cultured HCs were resuspended at $1\times 10^6$ cells/ml in IMDM containing 15% Ig-depleted human AB serum and antibiotics (Sigma) (25 μg/ml neomycin or 60 μg/ml penicillin plus (100 μg/ml streptomycin). The cells were cultured in suspension at $37°$ C. either in small erlenmeyer flasks containing a magnetic bar or in rolling tubes. The cells were primed for IFN-α secretion by an incubation of 2 hours in presence of 100 IU/ml of IFN-α (recombinant, Endogen Inc., Woburn, Wash. USA) followed by infection with Sendai virus (150 HA/ml) (Spafas Inc., Preston, Conn. USA). After 18–20 hours, the culture was centrifuged and the supernatant was virally inactivated by lowering the pH to 2.0 (HCl) for at least 2 hours. The neutralized (NaOH) supernatant was sterile filtered and stored at $-40°$ C.

EXAMPLE 4
IFN-α Assay

The IFN-α content of supernatants was measured by ELISA using a commercial kit (Endogen Inc.) according to the manufacturer's instructions or the inventor's system prepared with purified sheep anti-IFN-α (Endogen Inc.). Briefly, microplate wells were coated overnight with sheep anti-IFN-α (5 μg/ml). After saturation of binding sites with PBS containing 0.25% casein, the supernatants diluted in PBS-0.25% casein were added and incubated for 1 hour at $37°$ C. After washing, the bound IFN-α was reacted with biotin-labeled (EZ-Iink, Pierce. Rockford, 11. USA) sheep anti-IFN-α. After washing, peroxydase-conjugated streptavidin was added (30 minutes at $37°$ C.) followed after washing by the ortho-phenylene diamine substrate. Optical densities were read at 490 nm. Recombinant IFN-α (Endogen Inc.) was used as standard. Both ELISA systems gave similar results.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process for producing ex vivo natural interferon α (nIFN-α), said method comprising the steps of:
    a) expanding under suitable conditions hematopoietic stem cells (HSCs) in culture;
    b) priming said HSCs for nIFN-α secretion by incubating said HSCs in IFN-α;
    c) infecting said hematopoietic stem cells (HSCs) in culture medium with Sendai virus; and
    d) culturing the HSCs of step c) for a time sufficient for said HSCs to produce natural IFN-α,
    wherein said HSCs produce more natural IFN-α when expanded according to step a), than HSCs that have not been expanded.

2. The method of claim 1, further comprising before step b) and after step a), a step of pooling expanded HSCs obtained from step a).

3. The method of claim 1, further comprising after step c), a step of collecting from the culture medium the natural nIFN-α obtained from step c).

4. The method of claim 1, wherein the HSCs are from cord blood.

5. The method of claim 1, wherein the HSCs are enriched in $CD34^+$.

* * * * *

UNITED STATES PATENT AND TRADEMARK OFFICE
CERTIFICATE OF CORRECTION

PATENT NO.    : 6,472,208 B1
DATED         : October 29, 2002
INVENTOR(S)   : Real Lemieux, Sonia Neron and Chantal Proulx It is certified that error appears in the above-identified patent and that said Letters Patent is hereby corrected as shown below:

<u>Title page,</u>
Item [54], should read
-- NOVEL METHOD TO PRODUCE HUMAN NATURAL INTERFERON-α --

Signed and Sealed this

First Day of April, 2003

JAMES E. ROGAN
*Director of the United States Patent and Trademark Office*